United States Patent [19]

Doshi et al.

[11] Patent Number: 5,652,148

[45] Date of Patent: Jul. 29, 1997

[54] METHOD AND APPARATUS FOR RED BLOOD CELL SEPARATION

[75] Inventors: Sonal R. Doshi, Springfield, Pa.; John K. McGeehan, Woodbury; Wai Tak Law, Sewell, both of N.J.

[73] Assignee: Actimed Laboratories, Inc., Burlington, N.J.

[21] Appl. No.: 49,862

[22] Filed: Apr. 20, 1993

[51] Int. Cl.$^6$ .................................................. B01D 21/01
[52] U.S. Cl. .................. 436/178; 210/723; 210/729; 422/101; 436/177; 436/527; 436/531; 436/534
[58] Field of Search .................. 436/524, 527, 436/531, 534, 63, 69, 169, 170, 175, 177, 178, 825, 827; 435/2, 7.25; 422/56, 73, 101; 210/702, 714, 723, 729

[56] References Cited

U.S. PATENT DOCUMENTS

| | | | |
|---|---|---|---|
| 3,462,361 | 8/1969 | Greenwalt et al. | 604/7 |
| 3,917,453 | 11/1975 | Milligan et al. | 435/15 |
| 4,005,187 | 1/1977 | Kilthau et al. | 436/500 |
| 4,053,420 | 10/1977 | Marx | 210/435 |
| 4,155,854 | 5/1979 | Marx | 210/435 |
| 4,157,323 | 6/1979 | Yen et al. | 522/84 |
| 4,238,334 | 12/1980 | Halbfoster | 210/679 |
| 4,250,257 | 2/1981 | Lee et al. | 422/56 X |
| 4,252,653 | 2/1981 | Beck et al. | 210/321.87 |
| 4,256,693 | 3/1981 | Kondo et al. | 422/56 |
| 4,258,001 | 3/1981 | Pierce et al. | 422/56 |
| 4,288,228 | 9/1981 | Oberhardt | 422/56 X |
| 4,330,299 | 5/1982 | Cerami | 422/61 X |
| 4,371,515 | 2/1983 | Chu | 436/544 |
| 4,416,777 | 11/1983 | Kuroda et al. | 436/177 X |
| 4,426,451 | 1/1984 | Columbus | 436/518 |
| 4,450,104 | 5/1984 | Jordan | 530/396 |
| 4,493,793 | 1/1985 | Chu | 436/501 X |
| 4,526,871 | 7/1985 | Avrameas et al. | 436/504 |
| 4,532,107 | 7/1985 | Siddiqi | 422/56 |
| 4,532,232 | 7/1985 | Larsson et al. | 502/403 |
| 4,554,257 | 11/1985 | Aladjen et al. | 436/519 |
| 4,587,102 | 5/1986 | Nagatomo et al. | 422/56 |
| 4,594,327 | 6/1986 | Zuk et al. | 436/514 |
| 4,605,629 | 8/1986 | Lange et al. | 436/166 |
| 4,659,658 | 4/1987 | McCarthy et al. | 435/34 |
| 4,678,757 | 7/1987 | Rapkin et al. | 436/169 |
| 4,678,814 | 7/1987 | Rembaum | 522/175 |
| 4,680,274 | 7/1987 | Sakai et al. | 436/512 |
| 4,693,985 | 9/1987 | Degen et al. | 436/531 |
| 4,753,776 | 6/1988 | Hillman et al. | 422/101 |
| 4,765,895 | 8/1988 | Schlueter et al. | 210/491 |
| 4,786,603 | 11/1988 | Wielinger et al. | 436/69 |
| 4,803,153 | 2/1989 | Shibata et al. | 435/2 |
| 4,810,394 | 3/1989 | Masuda | 210/767 |
| 4,816,224 | 3/1989 | Vogel et al. | 422/55 |
| 4,839,296 | 6/1989 | Kennedy et al. | 436/170 |
| 4,855,108 | 8/1989 | Masuda et al. | 422/56 |
| 4,861,705 | 8/1989 | Margel | 435/2 |
| 4,861,712 | 8/1989 | Bartl et al. | 435/13 |
| 4,870,005 | 9/1989 | Akiyoshi et al. | 422/56 X |
| 4,879,340 | 11/1989 | Moriguchi et al. | 525/54.2 |
| 4,883,764 | 11/1989 | Kloepfer | 436/63 |
| 4,906,439 | 3/1990 | Grenner | 422/56 |
| 4,910,150 | 3/1990 | Doeding et al. | 436/69 |
| 4,917,799 | 4/1990 | Masuda et al. | 210/435 |
| 4,933,092 | 6/1990 | Aunet et al. | 422/101 X |
| 4,940,668 | 7/1990 | Wardlaw et al. | 436/174 |
| 4,946,603 | 8/1990 | Laugham et al. | 436/177 X |
| 4,987,085 | 1/1991 | Allen et al. | 436/169 |
| 4,990,457 | 2/1991 | Tanaka et al. | 436/170 |

(List continued on next page.)

*Primary Examiner*—Jill Warden
*Attorney, Agent, or Firm*—Iver P. Cooper

[57] ABSTRACT

Red blood cells are removed from whole blood or a fraction thereof by contacting whole blood with a combination of an agglutinating agent and nucleating particles to form clusters of red blood cells. High molecular weight polyethylene glycol may be added further to enhance agglutination. The clusters of red blood cells are much larger than the size of individual red blood cells, so that the clusters can easily be filtered through a porous medium. The plasma which is substantially free of red blood cells is further passed through a filter that optionally contains an additional agglutinating agent.

7 Claims, 2 Drawing Sheets

U.S. PATENT DOCUMENTS

| | | | |
|---|---|---|---|
| 5,055,195 | 10/1991 | Trasch et al. | 436/177 X |
| 5,064,541 | 11/1991 | Jeng et al. | 422/101 X |
| 5,110,550 | 5/1992 | Schlipfenbacher et al. | 422/56 |
| 5,118,428 | 6/1992 | Sand et al. | 210/749 |
| 5,135,719 | 8/1992 | Hillman et al. | 422/101 |
| 5,169,789 | 12/1992 | Bernstein | 436/501 |
| 5,262,067 | 11/1993 | Wilk et al. | 422/101 X |
| 5,411,870 | 5/1995 | Law et al. | 435/11 |

METHOD AND APPARATUS FOR RED BLOOD CELL SEPARATION

BACKGROUND OF THE INVENTION

1. Field of the Invention

The present invention relates to a method and apparatus for separating red blood cells from whole blood.

2. Description of the Background Art

The ability to measure a wide variety of physiologically active compounds, both naturally occurring and synthetic, has become of increasing importance, as an adjunct to both diagnosis and therapy. While for the most part such assays have required clinical laboratory determinations, there is an increasing awareness of the importance of being able to conduct assay determinations in a physician's office or in the home. These environments require that the assay have a simple protocol and be relatively free of sensitivity to small changes in the conditions under which the assay is carried out. Importantly, inaccurate measurements of reagents and samples should, whenever feasible, be avoided. A number of systems have been developed to address the various problems associated with analysis outside of the clinical laboratory.

One analyte of importance is cholesterol. There is a clearly established relationship between total blood cholesterol (mainly the LDL fraction) and coronary artery disease (*J.A.M.A.* 253: 2080–2086, 1985). New guidelines have been established for adults to identify risk groups associated with blood cholesterol level. Since cholesterol levels can be controlled by both diet and cholesterol lowering drugs, for those individuals at risk the ability to monitor one's own cholesterol at home is useful in reducing the potential for heart disease. The measurement of other naturally occurring compounds of physiological importance, such as glucose, lipoproteins, etc., as well as synthetic drugs, is also of great interest.

In clinical assays, the separation of serum or plasma from whole blood is extremely important since it is often difficult to conduct the analysis of dissolved blood components without interference from the red blood cells. Serum or plasma is conventionally separated from erythrocytes by centrifuging. Centrifugation, however, causes other problems because one must then separate the supernatant from the blood cake. Moreover, this method is not available for use in home or office diagnostic assays.

Using whole blood with diagnostic devices for use in home or office assays gives rise to further problems. In these devices, it is customary to employ reagents which cause a color change if the analyte is present (or, alternatively, if it is absent). Turbid or colored solutions, such as whole blood, may interfere with the readings.

Means for the fractionation of whole blood into blood cell plasma fractions are known in the art.

Vogel et al., in U.S. Pat. No. 4,464,254, disclose a process for separating plasma or serum from whole blood using a filter of glass fibers. The glass fibers used have an average diameter of 0.2 to 5 microns, and a density of about 0.1 to 0.5 g/cm. Whole blood is placed onto a layer of glass fibers, and plasma is generated by retardation of flow of the cells. Plasma is collected at the other side of the glass fibers.

Another approach to separating red blood cells from whole blood is shown in Hillman et al., U.S. Pat. No. 4,753,776. In this patent, capillary action is used to pull whole blood through a glass microfiber filter by retarding the flow of the cells.

Allen et al., in U.S. Pat. No. 4,987,085, disclose a device and method for separating plasma from whole blood via a filtering system with descending pore size to provide for successive removal of red blood cells without lysis. A combination of glass fiber membranes and cellulosic membranes is used to minimize red blood cell lysis while removing red blood cells.

Kondo et al., in U.S. Pat. No. 4,256,693, disclose a multilayered integral chemical analysis element for blood comprising a filter layer capable of removing formed components from the blood. The filter layer may be made of at least one component selected from paper, nonwoven fabric, sheet-like filter material composed of powders or fibers such as man-made fibers or glass fibers, and membrane filters having suitable pore sizes. The filter layer separates the formed components of the blood at one time, or successively, such as in the order of leukocytes, erythrocytes, and platelets.

Other filtration systems are described in U.S. Pat. Nos. 3,092,465; 3,630,957; 3,663,374; 4,246,693; 4,246,107; 2,330,410. Some of these filters employ membranes with small pores. A disadvantage of these filters is that blood can only penetrate through the membrane filter very slowly, and in small amounts because the membrane is very easily blocked. This results in a reaction which takes longer than is desirable.

Unfortunately, blood separation devices using glass fiber filters or membranes tend to retain significant amounts of serum or plasma, and display a relatively slow speed of separation. This presents a problem with diagnostic devices which are quantitative, as there must be sufficient sample present in the detection area to provide a reliable indication of the quantity of analyte detected. If insufficient sample flows through the filter, a false low reading will be obtained. Moreover, devices intended for home or office use should be convenient to use and should provide an indication of the analyte within a reasonably short period of time. It is thus essential to remove unwanted red blood cells to allow most of the remainder of the blood to pass through the separation device, and then filter the blood relatively quickly.

To solve these problems, test papers have been coated with semi-permeable membranes (U.S. Pat. No. 3,092,465), and swellable films into which only the dissolved components of the blood can penetrate, leaving the erythrocytes (U.S. Pat. No. 3,630,957). These two methods are only useful for testing for low molecular weight components of blood, such as glucose or urea. Higher molecular weight components of the blood such as lipids, or substrates bound to serum protein, such as bilirubin, cannot be determined in this way because they are not able to penetrate into the film or to pass through the semipermeable membrane.

Alternative solutions include covering diagnostic agents with membrane filters for separating the blood cells, as disclosed in U.S. Pat. Nos. 3,663,374 and 4,246,693. A disadvantage with these diagnostic agents is that the blood can only penetrate through the membrane filter very slowly and in small amounts, because the membrane is very easily blocked up. This results in a reaction which takes longer than is desirable.

U.S. Pat. Nos. 4,246,107 and 2,330,410, teach that lymphocytes and leukocytes can be separated from blood when blood is filtered through a layer of synthetic resin fibers with an average fiber diameter of from 5 to 20 microns for lymphocytes, and from 3 to 10 microns for leukocytes. However, since the erythrocytes preponderantly pass through the filter with the plasma, these filters are not suitable for obtaining plasma.

Red blood cells can also be removed from whole blood samples by contacting a whole blood sample with an agglutinating agent. One type of RBC agglutinating agent is a lectin, a family of sugar-binding proteins first identified in plants. Red blood cells can be removed from whole blood by contacting the whole blood with a lectin, which attaches itself to specific glycoproteins on the red blood cell membrane and forms large masses by agglutination of the cells. However, when lectins contact red blood cells, cross-linking occurs to form a gel. The presence of this gel in a filter greatly reduces the flow of blood through a filter, and therefore limits the amount of plasma recovered.

Sand et al., in U.S. Pat. No. 5,118,428, disclose using an acid, such as citric, acetic or ascorbic acid, to agglutinate the red blood cells for separation from whole blood. However, use of an acid lowers the pH of the plasma, which may interfere with subsequent analyses.

Trasch et al., in U.S. Pat. No. 5,055,195, disclose the use of erythrocyte-retention substrates which contain two strongly polar groups which are connected by a non-polar bridge which serves as a spacer. These substrates change the polarity of the surface of the erythrocytes and cause them to agglutinate. The agglomerates formed in the blood can then be readily separated by filtration.

Zuk, in U.S. Pat. No. 4,594,327, teaches a method for separating red blood cells from whole blood by combining the whole blood sample with a red blood cell binding agent. This mixture is then filtered through a solid bibulous agent.

Rapkin et al., U.S. Pat. No. 4,678,757, disclose a method for separating blood into fluid and cellular fractions for diagnostic tests. The whole blood is introduced into a carrier containing a layer of carbohydrate, which separates the fluid from the cellular fractions.

Hillman et al., in U.S. Pat. Nos. 4,753,776 and 5,135,719, disclose a method for separating plasma from red blood cells wherein a low-pressure filter is interposed in a pathway between an inlet port and a reaction area. Capillary force is the sole driving force for the movement of plasma from the filter to the reaction area. The filter is made of glass microfiber filters which can operate in the presence or absence of agglutinins.

A device for separating plasma or serum from whole blood is disclosed in Aunet et al., U.S. Pat. No. 4,933,297. This device consists of a matrix of hydrophilic sintered porous material with at least one red blood cell agglutinating agent incorporated therein. An optional filter containing the same agglutinating agent is added to give a filter combination that yields plasma which is about 97% free of red blood cells.

Laugharn et al., in U.S. Pat. No. 4,946,603, describe the use of a filter matrix which presents an overall negative surface electrical charge to whole blood to separate cells from plasma or serum.

Jeng et al., in U.S. Pat. No. 5,064,541, describe a filter means to retain blood cells which pass through a matrix of hydrophilic sintered porous material to which at least one red blood cell agglutinating agent has been applied. The agglutinating agents used include natural and synthetic water soluble polymers including hexadimethirine bromide, polylysine, and anti-red blood cell antibodies. The agglutination process is enhanced by incorporating substances such as polyvinyl pyrrolidone which functions as a dielectric, allowing charged cells to approach one another and by crosslinking by antibody and/or other agglutinins.

However, despite many attempts by prior workers to provide means to separate red blood cells from whole blood quickly and efficiently, there are still many disadvantages to the known methods, as described above. (No admission is made that any reference cited above constitutes prior art).

SUMMARY OF THE INVENTION

The present invention provides an efficient and rapid means for removing red blood cells from a blood sample. This method can be used in conjunction with an assay device for use in a physician's office or the home, as the red blood cells are rapidly removed from whole blood while most of the serum or plasma passes through the device for subsequent analysis.

The device provides cluster forming means made of a porous material such as an absorbent pad which contains therein both agglutinating agents and nucleating particles. These cooperate synergistically to rapidly agglutinate RBCs, allowing use of high flow rates while still achieving a substantially complete removal of RBCs. The agglutinating agent can be conjugated to the nucleating particles, or can be mixed with the nucleating particles. Red blood cells are agglutinated and trapped by the pad, while plasma flows through. It is believed that the agglutinating agent binds red blood cells, forming agglutinates thereof, while the nucleating particles provide a nucleus for formation of clusters of the agglutinates. However, it should be understood that the practice of this invention is not dependent on the correctness of this theory.

In one embodiment of the present invention, high molecular weight polyethylene glycol (MW>10,000) is added to the combination of agglutinating agent and nucleating particles. The polyethylene glycol enhances the formation of clusters.

The blood separation means of the present invention has the following features and advantages:

(1) Since whole blood can be directly used as a sample for assay, the processing operation is very simple and convenient. There is no requirement to separate the red blood cells from the sample prior to conducting the assay. Furthermore, the preparation time up to the chemical analysis per se is very short. Despite this, the red blood cell separating means of this invention can permit dry-chemical analysis of blood with accuracy equivalent to wet-method chemical analysis of components dissolved in blood using serum or plasma as a sample.

(2) The sample fluid resulting from the filtration of formed components from the whole blood transferred to the porous material is supplied smoothly to the analysis area of an assay device. Because the whole blood travels through the absorbent pad and secondary filter rather rapidly and most of the liquid traverses the red blood cell removing means, an accurate determination can be made of the analyte of interest.

DETAILED DESCRIPTION OF THE PREFERRED EMBODIMENTS

Blood is composed of two parts: (a) plasma, the fluid portion; and (b) formed elements, the blood cells and platelets suspended in the fluid. The plasma accounts for about 55% of the total volume of blood, and is about 92% water, 7% protein, and less than 1% other substances. The principal plasma proteins are the globulins, albumin, and fibrinogen. Plasma from which fibrinogen has been removed is called serum. The suspended particles include erythrocytes (red blood cells), leukocytes (white blood cells), and thrombocytes (platelets). Most of the blood cells (corpuscles) are red blood cells. White blood cells are larger than red blood cells, but fewer in number.

For purposes of the instant invention, the term "whole blood" indicates the original, untreated sample, and "blood" indicates plasma which still contains a substantial number of red blood cells, even if some red blood cells had previously been removed. The removal of red blood cells from a whole blood sample is a form of blood fractionation. Blood fractionation is important in clinical chemistry because chromogenic analysis is generally used to determine the concentration of particular components dissolved in blood. The presence of a particular component is signaled by color production or color change. The presence of red blood cells in whole blood disturbs the reading of the chromogenic analysis due to the turbidity and color of the whole blood. Therefore, it is important to remove red blood cells from whole blood prior to using the remaining serum or plasma in the analysis of dissolved blood components.

Thus, it is desirable to provide means for removing substantially all of the red blood cells from a sample of whole blood. For purposes of this invention, a sample is considered to be substantially free of red blood cells when any red blood cells that may remain in the sample do not interfere with the accuracy of the analysis for the analyte sought to be detected in the sample. That is, any red blood cells that may remain in the sample are not detectable by or do not interfere with the analytic method employed for detection of the analyte of interest.

Cluster Forming Means

The cluster forming means comprises any suitable material through which plasma or serum can pass, which is inert to whole blood and which does not interfere with subsequent assays of the blood sample, in combination with at least one agglutination agent and nucleating particles. A particularly useful cluster forming means is an absorbent pad which contains a combination of agglutinating chemicals and nucleating particles. Pads made from materials such as glass or synthetic fibers can be used. The pads can be woven or nonwoven. The fibers are preferably hydrophilic, either by the nature of the fibers themselves or by post-treatment of the fibers. The fiber size is not material.

The mesh or pore size of the pad should average about 200 microns, with a preferred range being from about 20 to about 500 microns.

The clusters formed range in size from about 100 to about 1500 microns. Most clusters fall into the range of from about 250 microns to 1000 microns.

One particularly suitable material for the absorbent pad is ORLON® acrylic fibers in a pad approximately ⅛ inch thick, with an average pore size of about 200 microns. Agglutinating chemicals and nucleating particles are incorporated into the absorbent pad by impregnation thereof, and the pad is subsequently dried. Optionally, an anticoagulant is used in the absorbent pad, e.g., EDTA or sodium heparinate.

In another embodiment, high molecular weight polyethylene glycol is also incorporated in the pad. Table 1 shows ranges for combinations of agglutinating agents and nucleating particles that can be used in the present invention. In Table 1, the rate of agglutination was rated from 1 to 4, with 4 being the fastest and 1 being the slowest. The concentration of each component is expressed in terms of the impregnating solution. Lectin is present in each experiment.

TABLE 1

1a) Effect of lectin concentration (*Phaseolus vulgaris*) on agglutination rate

| Lectin conc. (ug/mL) | 0 | 100 | 200 | 300 | 400 |     |
|---|---|---|---|---|---|---|
| Agglutination rate | 1 | 3 | 4 | 4 | 4 |     |

1b) Effect of nucleating particle (polyacrolein/iron oxide) concentration on agglutination rate

| Particle conc. (mg/mL) | 0 | 22 | 44 | 66 | 88 |     |
|---|---|---|---|---|---|---|
| Agglutination rate | 2 | 4 | 4 | 4 | 4 |     |

1c) Effect of molecular weight of PEG on agglutination rate

| MW of 5% w/v PEG | 6000 | 8000 | 10000 | 20000 | 35000 | 40000 |
|---|---|---|---|---|---|---|
| Agglutination rate | 1 | 1 | 2 | 4 | 4 | 4 |

The concentrations of agglutinating agent and nucleating agent are chosen so as to form clusters from substantially all of the red blood cells in a sample. Typically, the agglutinating agent will be present in a concentration ranging from about 10 to 400 micrograms/mL, and the nucleating particles will be present in a concentration of from about 0.1 to about 20 mg/mL. Where optional polyethylene glycol is used with the agglutinating agent, the polyethylene glycol is used in concentrations of approximately 0.1 to 30% w/v solution.

A buffered solution may be used to impregnate the absorbent pad with the agglutinating agent and nucleating particles and, where used, polyethylene glycol. This buffer may include phosphate buffered saline, tris, MOPS, borate, carbonate, or the like. Usually, the solution is buffered to a pH in the range of about 4 to 9. The concentrations of agglutinating agent, nucleating particles, and polyethylene glycol in the buffered solution are about 10 to 400 micrograms/mL, 0.1 to 20 mg/mL, and 0.1 to 30% w/volume, respectively.

In the case of the cholesterol assay, as illustrative of other assays, the impregnating solution has from about 2 to 100 units/ml of the two enzymes, cholesterol esterase and cholesterol oxidase. The detergents, if used, have total weight of from about 0.1 to 5 weight percent of the medium. The binding agents or adhesives are generally in the range of about 0.2 to 10 or more, usually from about 1 to about 5 weight percent of the total detergent mixture. A preservative or hydrogen bonding agent may be present in from about 1 to 20 weight percent, more usually from about 2 to 10 weight percent. The remaining additives are generally present in a total amount of less than about 10 weight percent. The remaining composition may be water, nonreactive ingredients, excipients, extenders, and the like.

Agglutinating Agents

Although many agglutinants for red blood cells are known, the agglutinants used must be such that they do not interfere with any subsequent analysis. Preferably, the agglutinating agents have fast action and a short re-activation time from the dry to the wet state, are nonspecific to blood types, and are stable and inexpensive. Agglutinating agents can readily be selected by screening tests with whole blood samples, which is well within the skill of the art.

The preferred agglutinants are lectins, including concanavalin A, wheat germ agglutinin, and the agglutinins of *Glycine max*, and *Phaseolous vulgaris* either separately or in combination. Lectins are proteins, widely distributed in nature, which are able to agglutinate erythrocytes and many other types of cells. More specifically, the term "lectin" denotes "a sugar-bonding protein or glycoprotein of non-immune origin which agglutinates cells and/or precipitates glycoconjugates," Goldstein et al., *Nature* 285:66 (1980). Lectins occur primarily in plant seeds, but they also occur in roots, leaves and bark. In addition, lectins are present in invertebrates such as clams, snails, and horseshoe crabs, and in several vertebrate species.

Members of the lectin family include concanavalin A, abrin, ricin, as well as soybean agglutinin and wheat germ agglutinin. Further background on lectins can be found in H. P. Schnebli and J. Bachi, "Reaction of Lectins with Human Erythrocytes", *Expt. Cell Research*, 91 (1975); and "Lectins and Lectin Conjugates", a general lectin catalogue produced by EY Laboratories, Inc., San Mateo, Calif., 1992.

Alternatively, antibodies can be used as agglutinating agents. The antibodies used have a binding affinity for a determinant present on the surface of red blood cells. Antibodies reactive with any antigen present on the surface of a red blood cell can be used, including but not limited to major histocompatibility antigens, cell surface proteins, cell surface carbohydrates, and cell surface glycoproteins. Antibodies for agglutinating erythrocytes are well known, and may be based upon antibodies which recognize various antigenic surface constituents of the erythrocytes, including proteins, glycoproteins, glycolipids and lipoproteins. Antibodies which recognize these constituents may be prepared by conventional techniques using the membrane, or the purified constituents themselves, as immunogens. These antibodies may be monoclonal or polyclonal in nature. Either the intact antibody, or specific binding fragments thereof, may be used as agents to agglutinate the erythrocytes.

It has also been discovered that polyethylene glycol can be added to the combination of the agglutinating agent and nucleating particles to enhance formation of clusters from red blood cells. As shown in Table 1 above, the agglutination rate is enhanced by the addition of polyethylene glycol having a molecular weight above 10,000. It was found that polyethylene glycol having a molecular weight of about 35,000 was particularly suitable, but that polyethylene glycol having molecular weights above 35,000 can also be used. The polyethylene glycol can be incorporated in the pad in the same manner as the agglutinating agent and nucleating particles, preferably by impregnation from a solution thereof.

Further discussion of erythrocyte agglutinating and binding materials is given in Hillyard et al., U.S. Pat. No. 5,086,002, which patent is hereby incorporated by reference in its entirety.

It is desirable that the agglutinating agent be capable of agglutinating all red blood cells of the species, e.g., human, to which the subject belongs. If a single monoclonal antibody is not available which is not serospecific, one may use a polyclonal antiserum against human red blood cells, or a defined mixture of monoclonal antibodies that collectively react with all of the major blood types. The antibody can be coated onto the nucleating particle, or can be slurried or dissolved in a suitable liquid for impregnation into the absorbent pad. There is generally a minimum amount of antibody that must be used in the blood separation device in order to remove substantially all of the red blood cells from the whole blood. However, it is not possible to give a specific amount of an antiserum that must be used, since different antisera differ in their ability to bind red blood cells.

Accordingly, the optimum amount of antibody is determined empirically, which can readily be effected by one skilled in the art. Serial two-fold dilutions of neat antibody-containing solution or antiserum are applied to filters along with the desired nucleating agents in an amount sufficient to saturate the filter. Efficiency of filtration, lysis of red blood cells, and amount of plasma that passes through the filter when a standard amount of whole blood is applied are measured.

Other types of agglutinating agents for red blood cells include polymeric amino acids such as polylysine, polyarginine, and the like.

Nucleating Particles

The nucleating particles for use in the present invention are particles which are capable of acting as nucleating agents and which do not react with any of the components of the blood to interfere with subsequent assays. These particles have an average diameter of from about 0.1 micron to about 100 microns, and preferably less than about 10 microns in diameter. When the particles are much greater in diameter than 100 microns, it is difficult to impregnate the particles into the pad matrix. Ideally, the nucleating particles are the same size or smaller than the red blood cells themselves.

Particles useful in the present invention are those which absorb lectins or other agglutinating agents on the surfaces of the particles. For example, the porous iron oxide particles used herein are magnetizable polyacrolein beads which contain iron oxide. These beads have reactive aldehyde groups on the surface thereof which link with lectins upon contact. Alternatively, the lectin or other agglutinating agent can be chemically immobilized onto the surface of the nucleating particles. Nonlimiting examples include lectin which has been immobilized onto silica, or lectin immobilized onto agarose. These nucleating particles with agglutinants on their surfaces thus allow red blood cells to agglutinate around them to form large clumps, or clusters.

Many other inert particles that permit absorption or immobilization of lectins or other agglutinating agents on their surfaces can also be used as nucleating particles in the present invention. Among these particles are latex beads, cellulose, titanium dioxide, polyacrolein, alumina, iron oxide, chromium oxide and the like.

For the purposes of the present invention, the preferred nucleating particles are polyacrolein or polyacrolein/iron oxide beads. However, as shown in Table 2, many types of particles can be used, and the invention is not limited to any specific particles. Additionally, combinations of nucleating particles can be used, in any desired proportions.

TABLE 2

Relative agglutination rate enhancement of different nucleating particles

| Particle | Relative agglutination rate |
| --- | --- |
| free lectin | 1 |
| free lectin + silica | 1 |
| lectin attached to polyacrolein bead | 2 |
| lectin attached to 0.3 micron latex | 20 |

The Secondary Filter

Optionally, a secondary filter is used to trap any extra red blood cells that escape from the absorbent pad. This secondary filter may be made of any filtration material which is compatible with the assay and which is capable of separating red blood cells from plasma. For example, it can be made of glass fiber paper, filter paper, or synthetic filter materials such as porex filter. The secondary filter should ideally have a very small pore size to permit plasma to pass but to retain any residual red blood cells. Ideally, a porous matrix with pore sizes between 1 and 5 microns can be used. A glass fiber filter with a mean pore size of 1.2 microns and a thickness of 737 microns is preferred, although a much thinner porous filter can also be used. Conveniently, when a secondary filter is provided, it is configured as the second layer of a two layer device.

Reagent Means

The red blood cell separating means can be used with any assay device which includes a reactant pad through which fluid flows to produce a detectable signal. After addition of the sample to the reactant pad through the red blood cell separation means, and an incubation of up to about 30 minutes, the analyte reacts with the reagents in the reactant pad to produce a detectable signal.

The red blood cell separation device can, of course, be used with assay devices for a great variety of substances in the blood in addition to cholesterol, including glucose, blood urea nitrogen, uric acid, albumin, creatinine bilirubin, phosphate, total protein, amylase, calcium, etc.

The red blood cell removing means of this invention can be used with any type of assay that can be conducted using a reactant or reagent zone for reaction with the analyte of interest. A variety of sophisticated reagents, protocols or regimens can be devised based upon a limited amount of material migrating to produce a boundary in proportion to the amount of material present. Examples of protocols include particles having first and second ligands, where the first ligand competes with analyte for receptor bound to a surface. After carrying out competition for a limited amount of receptor between analyte and particle, an aliquot of the assay medium is transferred to the sample pad and the particle transported with the effluent through the measurement region. By having receptor for the second ligand in the measurement region, the particle boundary will be defined by the number of particles added to the pad. By having colored particles, charcoal particles, magnetic particles, dyes, dye-polymer conjugates, protein with high visible extinction coefficients, etc., the boundary will be readily defined.

Any technique which allows for binding of a detectable entity in proportion to an analyte of interest may be employed. These may include cleavage of a bond to release the entity, where the bond to the entity is not clearable when the entity is bound to a receptor, binding to a support which inhibits migration of the entity in proportion to the amount of analyte in a sample, or the like. The entity may be a particle as described above, an enzyme which catalyzes the production of a detectable product, or the like.

Of particular interest is where a product is produced on the sample pad which provides for a detectable boundary. For example, where the analyte is an enzyme substrate, the sample pad may be impregnated with the appropriate enzyme or enzymes to provide for a product. Normally, the enzyme product will react, either directly or indirectly, with a compound which is fixed in the assay measurement region. This may be exemplified by cholesterol, glucose, or the like, which reacts with an oxidase to provide an oxidizing species. The oxidizing species may then react with the bound compound to produce a detectable boundary. Illustrative of this situation would be the hydrolysis of serum cholesterol ester by cholesterol esterase and subsequent oxidation of cholesterol by cholesterol oxidase to produce a stoichiometrically identical amount of hydrogen peroxide. This hydrogen peroxide is formed at a stationary reaction pad and combines with horseradish peroxidase which is in the mobile phase. The horseradish peroxidase/hydrogen peroxide reacts with a bound substrate to produce a detectable boundary.

Depending upon the assay, other reagents may also be present. For example, detergents can be used where a lipophilic analyte in blood is involved, where the lipophilic analyte binds to proteins bound to blood. This may be illustrated by cholesterol which binds to proteins, as for example, in very low, low and high density lipoproteins. Thus, detergents such as nonionic, anionic or cationic detergents may be used. Of particular interest are polyoxyalkylene, ethoxylated alkylphenol, octylphenoxypolyethoxyethanol, octylphenol-ethylene oxide condensates and polyoxyethylene lauryl ether, or anionic detergents; such as bile acids, e.g., sodium cholate and sodium taurocholate. In addition, various sticking agents or adhesives may be used, such as gum arabic. Also of interest are proteins which are substantially noninterfering, which may include gelatin, casein, serum albumin, or gamma globulins. In addition, the reagent pad may include preservatives, such as sucrose, polyvinyl alcohol, polyvinyl pyrrolidone, dextran, as well as catalase inhibitors such as sodium azide or hydroxylamine salts.

The Apparatus and Method

Figure 1:
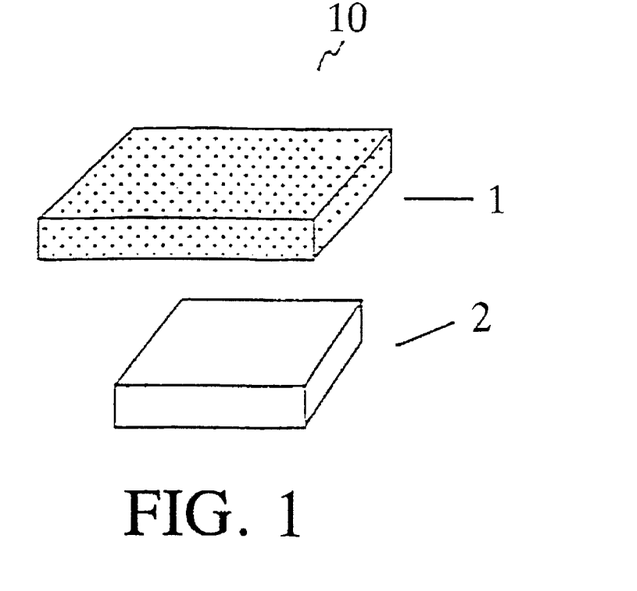
FIG. 1 shows a device according to the invention.

Red blood cells are rapidly removed from a sample of whole blood using the blood separation device 10 of the present invention as shown in FIG. 1. Whole blood is introduced to the absorbent pad 1, which absorbent pad is impregnated with an agglutinating agent and a nucleating agent. Most of the separation of red blood cells occurs in the absorbent pad, where the red blood cells are agglutinated into large clusters which are retained in the absorbent pad. The blood then rapidly passes into the secondary filter 2 for final separation of any left over red blood cells that may remain in the sample. Since white blood cells, which only occupy about 1% of the total volume of blood, are much larger than red blood cells, the white blood cells are trapped by the filter.

FIG. 1 illustrates one embodiment of the invention. When whole blood is introduced into the absorbent pad 1, the red blood cells contact the agglutinating agent and nucleating particles and agglutinate very quickly, e.g., in less than 5 seconds, into large clumps of cells. The clumps have an average diameter of about 500–1000 microns. The red blood cell aggregates remain in the absorbent pad because the pore size of the pad is small enough to retain the aggregates. The plasma, which is now predominantly free plasma, flows into the secondary filter 2. The secondary filter 2 traps any extra red blood cells that escape from the absorbent pad.

Figure 2:
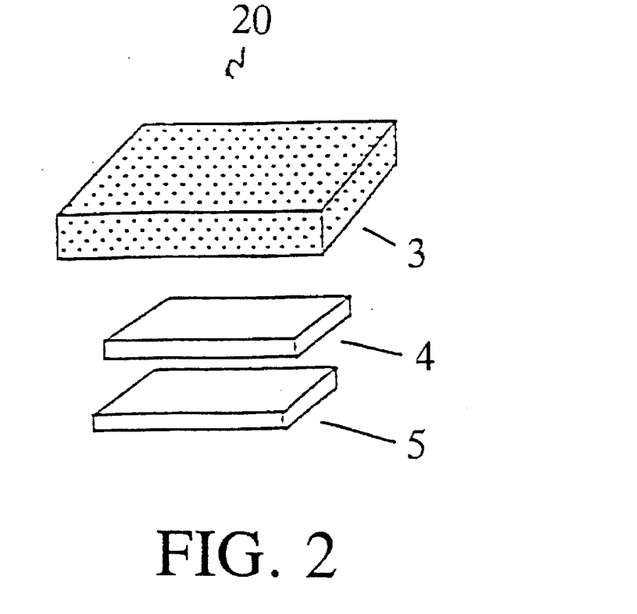
FIG. 2 shows a device according to the invention with an optional secondary filter.

FIG. 2 shows an optional third layer 3 which has an agglutinating agent deposited thereon. This third layer is present to ensure a plasma substantially free of red blood cells for particularly sensitive assays.

Figure 3:
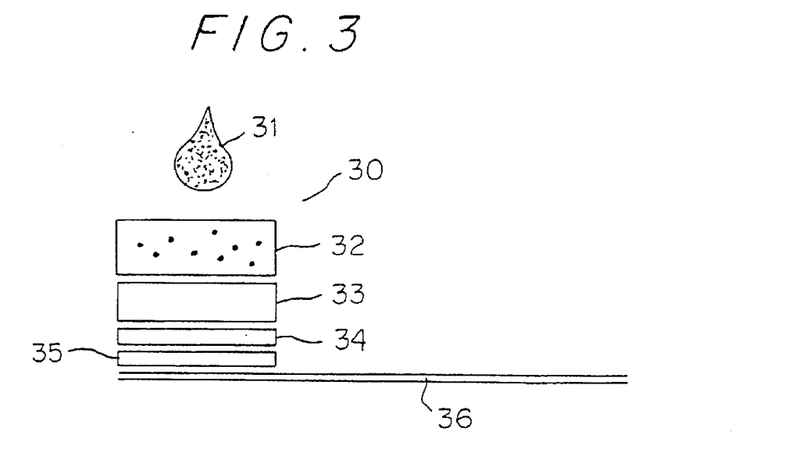
FIG. 3 shows the device according to the invention incorporated in a diagnostic device.

FIG. 3 shows an assay device 30 incorporating the blood separation means of the present invention. Whole blood 31 is introduced to the device through the absorbent pad 32. This absorbent pad is impregnated with beads of acrolein/iron oxide which have been coated with a lectin. Most of the red blood cells in the sample agglutinate almost immediately upon contact with the absorbent pad, and are retained in this part of device. Blood which is substantially free of red blood cells flows to the secondary separation pad 33. This pad is made of 1.2 micron glass fibers, and traps any red blood cells that were not agglutinated and retained in the absorbent pad. The sample then flows to the enzyme pad 34 that contains the cholesterol enzymes (cholesterol esterase and cholesterol oxidase). After cholesterol in the sample is converted to hydrogen peroxide, the sample passes through pad 35, the time delay pad, and finally contacts the measurement dye zone 36. The measurement dye zone 36 is coated or impregnated with an indicator material that reacts with the enzyme-treated sample to give an indication of the presence or amount of analyte in the sample.

Figure 4:
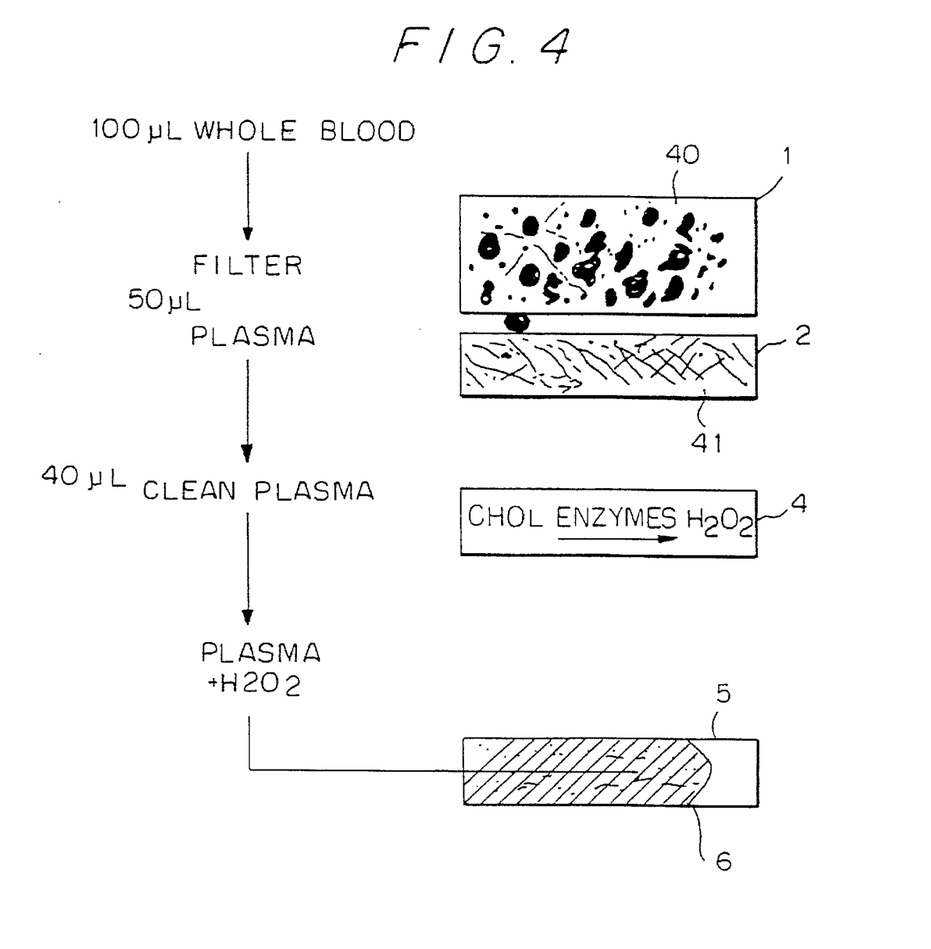
FIG. 4 is a schematic showing the operation of the device of FIG. 3.

FIG. 4 illustrates use of the device according to the present invention for a cholesterol determination. Of course, the device can be used with a great variety of clinical assays, and this illustration is not intended to limit the invention to one type of assay.

Referring to FIG. 4, a sample of whole blood, generally approximately 100 microliters, is introduced into an absorbent pad 1. The red blood cells present in the whole blood agglutinate into large (500-1000) clusters 40 around nucleating particles and are trapped in the absorbent pad. Any small clumps 41 that leak through the absorbent pad 1 with the plasma are trapped by the secondary glass fiber pad 2. Plasma then enters the enzyme pad 4. The enzyme pad is impregnated with cholesterol esterase and cholesterol oxidase. The cholesterol in the plasma reacts with these enzymes to produce hydrogen peroxide.

The hydrogen peroxide in the plasma then flows into the measurement zone 5 that contains a dye immobilized thereon. This dye reacts with hydrogen peroxide to form a color bar 6, the length of which is related to the amount of cholesterol in the sample.

The following examples illustrate the capacity of the device of the present invention to remove red blood cells from whole blood. These examples are included for purposes of illustration and comparison only, and are not intended to limit the scope of the invention.

EXAMPLE 1

The device shown in FIG. 1 (10) has an absorbent pad 1 made from ORLON® acrylic fiber from Lydall Westex with dimensions of 9.0 mm×6.1 mm×2.1 mm. A solution of 125 U/mL lectin in 5 mM phosphate buffered saline, pH 7.2, was made up. Seventy microliters of this solution was mixed with 1.4 mg of polyacrolein/iron oxide particles of size about 1-20 microns, with a mean particle size of 10 microns. The mixture was added to the pad, which absorbed the liquid. The pad was air dried for twelve hours at 70° F. and 5% relative humidity.

A secondary filter (2) was made from a glass fiber Whatman GD1 filter material cut to dimensions of 7.2 mm×5.5 mm×1.4 mm. This secondary filter was placed below the absorbent pad.

The device as prepared above was tested by depositing 140 microliters of whole blood having a hematocrit of 40-50% red blood cells onto the absorbent pad. The effectiveness of separation of red blood cells from whole blood was tried with a variety of agglutinating agents and nucleating agents. The speed of separation, the amount of plasma recovery, and the amount of red blood cell leakage are shown in Table 1. A rating of 0 RBC leakage represents no red blood cell leakage, and the plasma sample is visibly clear. A rating of 4 represents that the plasma recovered contained more than 20% red blood cells.

Conventional glass fiber pads did a poor job of separating 140 microliters of whole blood, as shown in row 1 of Table 2. Adding free lectin improved the plasma yield while also shortening the separation time. Lectin with nucleating particles (row 3) and lectin immobilized on silica (row 4) were found to be the most effective in giving clean, efficient, and fast plasma separation.

TABLE 3

| | YIELD OF PLASMA (uL) | SEPARATION TIME (sec.) | RBC LEAKAGE |
|---|---|---|---|
| 1. ABS.PAD + GD1 | 15 | 192 | 4 |
| 2. FREE LECTIN (GD1) | 25 | 25 | 0.5 |
| 3. LECTIN + BEAD (GD1) | 32 | 5 | 0 |
| 4. LECTIN ON SILICA (GD1) | 34 | 42 | 1 |

EXAMPLE 2

A separation device 20 as shown in FIG. 2 was prepared having an absorbent pad 1 made from ORLON® acrylic fibers from Lydall Westex with dimensions of 9.0 mm×6.1 mm×2.1 mm. A solution of 125 u/mL lectin in 5 mM phosphate buffered saline, pH 7.2, was made up. Seventy microliters of this solution was mixed with 1.4 mg of acrolein/iron oxide particles and the mixture was added to the pad, which absorbed the liquid. The pad was air dried for twelve hours at 70° F. and 5% relative humidity.

A secondary filter (2) was made from Whatman GD1 filter material cut to dimensions of 7.7 mm×5.5 mm×0.5 mm. This secondary filter was placed below the absorbent pad.

A third filter (3) was placed below the secondary filter. This third filter also had dimensions of 7.7 mm×5.5 mm×0.5 mm.

The absorbent pad in each trial was made of S&S Grade 5-S nonwoven rayon pads, S&S Grade 40 glass fiber pads, or S&S Grade 404 filter paper. Each absorbent pad was impregnated with 3 micrograms of free lectin in 0.5 mM PBS, pH 7.2 and air dried prior to assembling the device.

The devices were tested by depositing 140 microliters of whole blood having a hematocrit of 40-50% red blood cells onto the absorbent pad. The separation time, yield of plasma, and leakage of red blood cells are shown in Table 4, demonstrating that absorbent pads made of fibers other than glass were as effective as corresponding absorbent pads made of glass fibers.

TABLE 4

| | Yield of Plasma | Separation Time (sec.) | RBC Leakage |
|---|---|---|---|
| ABS.PAD + S&S40 + S&S5 – S | 40 | 20 | 0 |
| ABS.PAD + S&S40 + S&S404 | 29 | 19 | 0 |
| ABS.PAD + S&S5 – S + S&S404 | 26 | 20 | 0 |

EXAMPLE 3

In this example, lectins purified from *Phaseolus vulgaris* were used as in Example 1 to impregnate the absorbent pad. Lectins purified from *Phaseolus vulgaris* were found to be the most effective and the most non-specific for different blood types. The absorbent pads and the nucleating particles used were the same as in Example 2. In all cases, lectins in combination with nucleating particles decreased the separation times and increased plasma yield by approximately 30% when compared with results with free lectin alone. Lectins purified from *Phaseolus vulgaris* were found to be particularly effective for separating red blood cells from a variety of blood types. However, mixtures of two or more types of lectins have also been found useful in separating red blood cells. In all cases, lectins in combination with nucleating particles decreased the separation times by 3 to 5-fold when compared with the results with free lectins alone.

TABLE 5

|  |  | Yield of Plasma (μL) | Separation Time (sec.) | RBC Leakage |
|---|---|---|---|---|
| LECTIN | TYPE O | 25 | 25 | 0.5 |
| LECTIN + BEAD | TYPE O | 32 | 5 | 0 |
| LECTIN | TYPE A | 30 | 34 | 0 |
| LECTIN + BEAD | TYPE A | 30 | 7 | 0 |
| LECTIN | TYPE AB | 26 | 25 | 0 |
| LECTIN + BEAD | TYPE AB | 34 | 6 | 0 |

EXAMPLE 4

Using the assay device 30 shown in FIG. 3, two drops of whole blood from a finger stick 31 (approximately 100 microliters) are placed onto a cluster forming means comprising an absorbent pad 32 which had previously been impregnated with iron oxide particles and lectin as in Example 2. The red blood cells in the whole blood are agglutinated into clusters in the absorbent pad 32 and rapidly pass through secondary filter 33 and third filter 34 to remove substantially all of the red blood cells from the sample. This agglutination/filtration is accomplished in less than 10 seconds. The blood then contacts a pad 35 which has been impregnated with an enzyme which uses the analyte of interest as a substrate to form hydrogen peroxide, and the sample then contacts the measurement zone 36. As the hydrogen peroxide formed from the analyte in the sample enters the measurement zone 36, a color bar develops. The length of this color bar is proportional to the concentration of analyte in the sample.

Analytes which can be determined in a device according to this example are particularly those which form hydrogen peroxide upon contact with the appropriate enzyme. Among these analytes are cholesterol, glucose, uric acid, and the like.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All patents, patent applications, and other literature cited herein are hereby incorporated by reference.

What is claimed is:

1. A method for removing red blood cells from whole blood or a red blood cell-containing fraction thereof comprising:
    (a) contacting said whole blood or fraction thereof with a mixture of (i) free red blood cell agglutinating agent and (ii) nucleating particles to which red blood cell agglutinating agent is conjugated to form clusters of red blood cells, and
    (b) removing at least some of said clusters by filtration.

2. The method according to claim 1 wherein said agglutinating agent comprises at least one lectin.

3. The method according to claim 1 wherein said nucleating particles are selected from the group consisting of polyacrolein, polyacrolein/iron oxide, latex, silica, agarose beads, and mixtures thereof.

4. The method according to claim 3 wherein said nucleating particles are particles of polyacrolein/iron oxide.

5. The method according to claim 3 wherein said nucleating particles are particles of latex.

6. The method according to claim 1 wherein said whole blood or fraction thereof is also contacted with polyethyleneglycol having a molecular weight above about 10,000.

7. The method of claim 1 wherein said mixture is prepared by contacting nucleating particles with an excess of red blood cell agglutinating agent and wherein the nucleating particles are not washed to remove excess agglutinating agent prior to step (b).

* * * * *